United States Patent

Wilk et al.

[11] Patent Number: 5,749,376
[45] Date of Patent: May 12, 1998

[54] MEDICAL TREATMENT AND WASTE DISPOSAL METHOD

[76] Inventors: Peter J. Wilk, 185 W. End Ave., New York, N.Y. 10023; Charles L. Knoll, 52 Crescent Ave., Passaic, N.J. 07055; Eugene Wexler, 133 Lexington Ave., New, N.Y. 10016

[21] Appl. No.: 561,399

[22] Filed: Nov. 21, 1995

Related U.S. Application Data

[63] Continuation-in-part of Ser. No. 138,405, Oct. 18, 1993, abandoned.

[51] Int. Cl.⁶ .................................................. A61B 19/00
[52] U.S. Cl. ......................... 128/898; 604/49; 604/51; 128/919; 128/917; 422/901
[58] Field of Search ................... 604/110, 28, 49, 604/51, 52, 53, 54, 55, 56, 265, 280, 264; 606/154, 156, 222, 223, 224, 230, 231, 139; 128/898, 917, 919; 206/365, 366, 364, 363, 367, 368, 369, 380, 370, 205, 207, 210, 524.5; 422/901

[56] References Cited

U.S. PATENT DOCUMENTS

| | | |
|---|---|---|
| 387,454 | 8/1888 | Siegenthaler . |
| 3,358,684 | 12/1967 | Marshall . |
| 4,664,256 | 5/1987 | Halskov . |
| 4,816,021 | 3/1989 | Johnson .................. 604/110 |
| 4,932,962 | 6/1990 | Yoon et al. ............... 606/224 |
| 4,936,835 | 6/1990 | Haaga ..................... 604/265 |
| 4,976,704 | 12/1990 | McLees .................... 604/272 |
| 4,981,149 | 1/1991 | Yoon et al. ............... 606/224 |
| 5,240,108 | 8/1993 | Tonna ..................... 206/364 |
| 5,322,165 | 6/1994 | Melker et al. ............. 206/365 |
| 5,323,719 | 6/1994 | Withers et al. ............ 206/366 |

FOREIGN PATENT DOCUMENTS

| | | | |
|---|---|---|---|
| 8803813 | 6/1988 | WIPO | .................. 422/901 |
| 9007348 | 7/1990 | WIPO . | |

*Primary Examiner*—Michael Powell Buiz
*Assistant Examiner*—Ronald K. Stright, Jr.
*Attorney, Agent, or Firm*—R. Neil Sudol; Henry D. COLeman

[57] ABSTRACT

A medical method utilizes a medical instrument such as a suturing needle made of biocompatible material. In addition, a medical operating room is provided with a container of a solvent fluidic material. During a medical procedure, the instrument is used to operate on a patient in the operating room. Upon completed use of the instrument, it is deposited in the container in the operating room, whereupon the instrument dissolves in the container.

10 Claims, 1 Drawing Sheet

5,749,376

MEDICAL TREATMENT AND WASTE DISPOSAL METHOD

CROSS-REFERENCE TO RELATED APPLICATION

This application is a continuation-in-part of U.S. patent application Ser. No. 08/138,405, filed Oct. 18, 1993 now abandoned.

BACKGROUND OF THE INVENTION

This invention relates to a medical method. More particularly, this invention relates to a medical method concerning the disposal of medical instruments. This invention also relates to a medical instrument utilizable in performing the method.

One of the major problems in conducting medical operations involves protecting the involved medical personnel from contamination from infected patients. Suturing and hypodermic needles are particularly troublesome owing to their small size and capability of transferring contagious bacteria or viruses from the patient to a physician, nurse or other assistant who may be inadvertently pricked with a used needle. In view of this danger, needles are scrupulously counted and tracked in the hospital operating room. Despite this high level of care, needles are frequently lost and therefore pose an unknown threat to hospital personnel and other patients, as well as people providing services to the hospital.

Home-care professionals and patients such as insulin-dependent diabetics, who perform hypodermic and/or intravenous procedures outside a hospital environment, face special challenges in the disposal of contaminated medical instruments, since they do not have available the elaborate disposal facilities of a large healthcare institution.

OBJECTS OF THE INVENTION

An object of the present invention is to provide a medical procedure which reduces, if not eliminates, danger of infection transfer from patient to medical personnel owing to contaminated medical instruments.

Another object of the present invention is to provide such a procedure or method which is particularly suitable for the hospital operating room and/or patients' individual hospital rooms.

Another, more particular, object of the present invention is to provide such a method which reduces, if not minimizes, the time and effort required by hospital personnel to dispose of used surgical instrumentation in the operating room.

Yet another object of the present invention is to provide a medical instrument such as a needle which is utilizable in practicing the method of the invention.

A further object of the present invention is to provide a medical procedure which can be performed in the home.

These and other objects of the present invention will be apparent from the drawings and detailed descriptions herein.

SUMMARY OF THE INVENTION

A medical method comprises, in accordance with the present invention, the steps of (a) providing a medical instrument made of biocompatible material, (b) also providing, in the same room as a patient, a container of a fluidic solvent material, (c) using the instrument to operate on a patient, (d) upon completed use of the instrument, depositing the instrument in the container in the room, and (e) dissolving the instrument in the fluidic solvent in the container.

A method in accordance with the present invention reduces, if not eliminates, danger of infection transfer from a patient to medical personnel, particularly in the hospital operating room. Instead of having a nurse, aide or other surgical assistant counting needles, for example, the surgeon merely deposits used needles in a container nearby. If the container is thus placed within arm's reach of the surgeon in the operating room, the number of people coming into contact with the contaminated needles is reduced.

A method in accordance with the present invention reduces, if not eliminates, danger of infection transfer from a patient to medical personnel regardless of where the patient is located, provided that a container of the solvent solution is nearby to enable an immediate disposal of a contaminated instrument such as a hypodermic needle. Ideally, nearly every hospital room would be provided with a container of the solvent material so that hypodermic needles, and other medical instruments such as the tips of indwelling catheters, can be immediately discarded and destroyed upon removal from the patient.

If the solvent or disposal solution contains an antibacterial agent and/or an antiviral agent, bacteria and viruses on the contaminated instrumentation may be destroyed in the container prior to discarding of the contents thereof upon termination of a medical operation. The solvent solution may be essentially sterile.

A medical operating technique or medical waste disposal method in accordance with the present invention reduces overall costs of hospitalization and surgery because of the facilitation of hospital surgical and disposal procedures.

DETAILED DESCRIPTION

Figure 1:
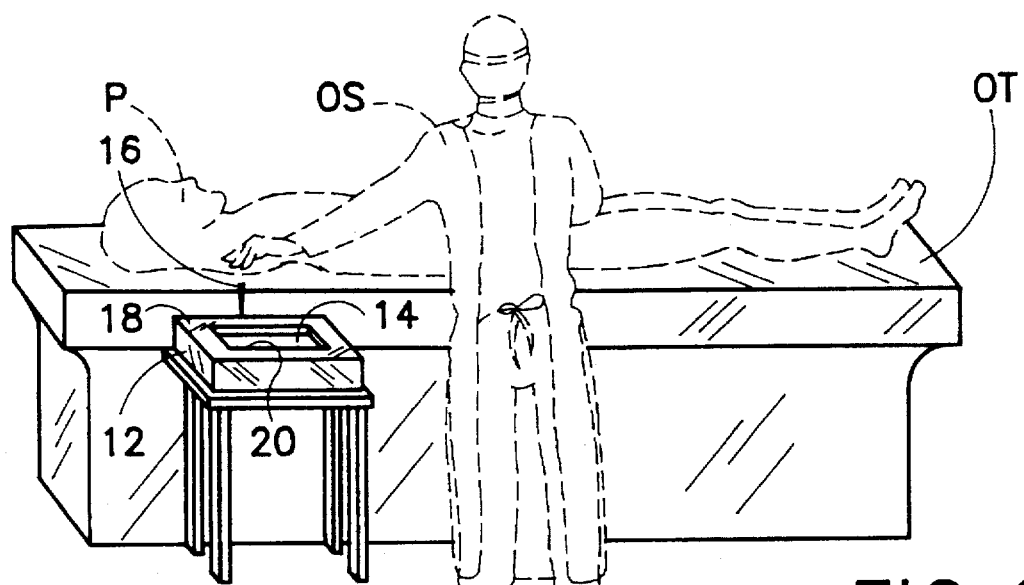
FIG. 1 is a schematic perspective view of an operating table in an operating room with a container for receiving used medical instruments or tools, showing use of the container in a method in accordance with the present invention.

As illustrated in FIG. 1, a container 12 holding a solvent fluid 14 is disposed beside an operating table OT in a hospital operating room. Table OT serves to support a patient P in the operating room during performance of a surgical procedure by a surgeon OS. Container 12 is disposed preferably within arm's length of the position of surgeon OS at table OT.

During the surgical procedure, surgeon OS uses one or more surgical instruments or tools, such as a suturing needle 16. Suturing needle 16 is made of a biocompatible material which can be dissolved by fluid 14 in container 12. When surgeon OS is finished using needle 16 on patient P, surgeon OS reaches to the side and deposits needle 16 in container 12. To that end, container 12 is provided in an upper surface 18 with an opening 20 for facilitating the introduction or deposition of needle 16, as well as other surgical instruments such as scalpels, in container 12.

Suitable biocompatible materials for needle 16 and other disposable operating instruments are well known to those in the field. Biocompatible polymeric materials include polymers and coploymers of carboxylic acids such as glycolic acid and lactic acid, polyamides such as nylon, polyacrylonitriles, polyphosphazines, polylactones such as polycaprolactone, and polyanhydrides such as poly[bis(p-carboxyphenoxy)propane anhydride] and polyehtylenes, polyvinyl chloride (PVC) and ethylene vinyl acetate. Other biocompatible materials which will dissolve readily in known solvent solutions as described herein are also well known to those skilled in the instrument design arts.

Fluid 14 is any fluid capable of dissolving or dispersing the material of used surgical needle 16. Solvents for polymeric materials are well known. For example, where needle 16 is made of a polyamide, fluid 14 may be a phenol, chloral hydrate, a mineral acid, formic acid, or other aqueous acids. Where needle 16 is made of a polyacrylonitrile, fluid 14 may be dimethyl formamide, dimethylacetamide, or an aqueous solution of sodium thiocyanate or nitric acid. Where needle 16 is a made of a polyvinyl chloride of high molecular weight, fluid 14 may be cyclohexanone, nitrobenzene, or tetrahydrofuran. For lower PVC polymers, fluid 14 may be toluene or ethylene chloride.

Of course, needle 16 may be made of a material other than a polymeric material. Materials useful for medical instrumentation are well known to those skilled in the art, and solvents for such materials can be readily found in standard references such as the *Encyclopedia of Chemical Technology* (John Wiley & Sons) and the *Polymer Handbook* (John Wiley & Sons).

To aid in the decontamination of used surgical instrumentation deposited in container 12, fluid 14 may include an antibacterial agent and/or an antiviral agent. Such agents include alcohols and glutyl aldehyde. Other agents suitable for this purpose are well known to those in the medical field.

Because surgeon OS merely deposits used needles 16 in container 12, without the necessity for intervention by operating room assistants, the danger of infection transfer from patient P to medical personnel in the operating room is reduced. The number of personnel handling contaminated surgical instruments, particularly needles 16, is reduced. Basically, such instruments are handled only by the surgeon. After use, they are deposited into container 12 for dispersion and discarding.

In some cases, particularly where fluid 14 is an aqueous solvent, fluid 14 and any surgical instruments dissolved therein may be disposed of into the sewage system, where fluid 14 is diluted by waste water.

Figure 2:
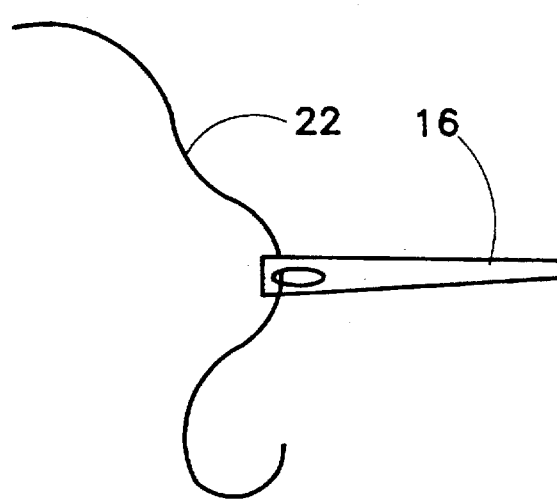
FIG. 2 is a side elevational view of a surgical needle with a suture, for use and subsequent disposal in a method in accordance with the present invention.

FIG. 2 illustrates surgical needle 16 with a suture 22 attached thereto, for use in a surgical procedure involving instrumentation disposal steps as discussed hereinabove. Needle 16 is made of a biocompatible polymeric material. The suture 22 may also be made of bioabsorbable and biocompatible material.

Figure 3:
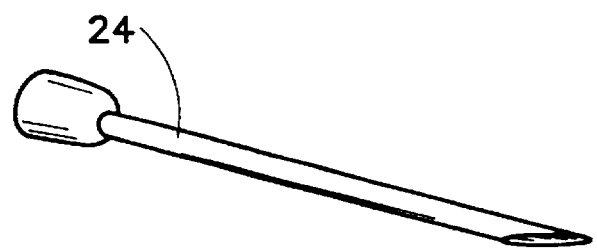
FIG. 3 is a perspective view of a hypodermic needle, for use and subsequent disposal in accordance with the present invention.

FIG. 3 illustrates a hypodermic needle 24 attachable to or preattached to a syringe (not illustrated). Hypodermic needle 24 is made of a biocompatible material for disposal through dissolution as described hereinabove with respect to surgical needle 16. Where hypodermic needle 24 is destined for home use, for example in the self-administration of insulin by a diabetic or for use by a home-care professional, a container 20 with dispersion fluid 14 may be provided in the home for immediate and sanitary disposal of needle 24. Needle 24 is inserted into container 20 following use of needle 24 in a hypodermic injection procedure.

Although the invention has been described in terms of particular embodiments and applications, one of ordinary skill in the art, in light of this teaching, can generate additional embodiments and modifications without departing from the spirit of or exceeding the scope of the claimed invention. For example, the disposal of needles as described above may be used for discarding and destroying hypodermic needles in patients' rooms, such needles being used to inject medication, for example, or to remove blood or other substances from a patient. An example of other instruments contemplated by the invention are biopsy needles or forceps. Upon withdrawal of a hypodermic needle from a patient, the needle is deposited into a dispersal solution as described above. Such solution may be held in a container in the patient's room, for example, on the wall.

Accordingly, it is to be understood that the drawings and descriptions herein are profferred by way of example to facilitate comprehension of the invention and should not be construed to limit the scope thereof.

What is claimed is:

1. A medical method comprising the steps of:

providing a medical instrument made of a biocompatible material;

also providing, in the same room as a patient, a container of a fluidic material which is a solvent for said biocompatible material, said container being other than or different from said patient;

using said medical instrument in a medical procedure on the patient in said room;

upon completed use of said instrument, depositing said instrument in said container in said room; and dissolving said instrument in said container.

2. The method defined in claim 1 wherein said instrument is a hypodermic needle, said step of using including the step of puncturing a skin surface of the patient with said needle.

3. The method defined in claim 2 wherein said step of using includes a step taken from the group consisting of extracting blood from the patient with said needle and injecting a substance into the patient with said needle.

4. The method defined in claim 1 wherein said instrument is a suturing needle, said step of using including the step of inserting a suture in organic tissues of the patient with said needle.

5. The method defined in claim 1 wherein said step of also providing includes the step of placing said container within arm's length of an operating table in said room.

6. A medical method comprising the steps of:

providing a medical instrument made of biocompatible material;

also providing a container holding a liquid substance;

using said instrument to operate on a patient, said container being other than or different from said patient;

upon completed use of said instrument, depositing said instrument in said container; and dissolving said instrument in said liquid substance in said container.

7. The method defined in claim 6 wherein said instrument is a hypodermic needle, said step of using including the step of puncturing a skin surface of the patient with said needle.

8. The method defined in claim 7 wherein said step of using includes a step taken from the group consisting of extracting blood from the patient with said needle and injecting a substance into the patient with said needle.

9. The method defined in claim 6 wherein said instrument is a suturing needle, said step of using including the step of inserting a suture in organic tissues of the patient with said needle.

10. The method defined in claim 6 wherein the patient and said container are disposed in the same room, said steps of using and depositing being performed by the same individual.

* * * * *